(12) United States Patent
Renz

(10) Patent No.: US 6,616,000 B1
(45) Date of Patent: Sep. 9, 2003

(54) INFANT FEEDING AND STORAGE SYSTEM

(75) Inventor: Charles John Renz, Briarcliff Manor, NY (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 10/126,470

(22) Filed: Apr. 19, 2002

(51) Int. Cl.[7] .............................. A61J 9/00; A61J 9/06; A61J 9/08; A61M 1/06
(52) U.S. Cl. .................... 215/11.1; 215/11.3; 215/11.6; 604/74
(58) Field of Search .............................. 215/11.1, 11.3, 215/11.6; 604/74

(56) References Cited

U.S. PATENT DOCUMENTS

| | | | | |
|---|---|---|---|---|
| 2,599,630 A | * | 6/1952 | Hair ........................... | 215/11.1 |
| 2,624,485 A | * | 1/1953 | Boston ....................... | 215/11.3 |
| 2,987,209 A | * | 6/1961 | Leonard ..................... | 215/11.3 |
| 3,851,781 A | * | 12/1974 | Marco ......................... | 215/11.6 |
| 3,977,405 A | | 8/1976 | Yanase | |
| 4,323,067 A | * | 4/1982 | Adams ........................ | 128/281 |
| 4,501,585 A | | 2/1985 | Friedman | |
| 4,573,969 A | | 3/1986 | Schlensog et al. | |
| 4,600,104 A | | 7/1986 | Yanase | |
| 4,705,504 A | | 11/1987 | Viers | |
| 4,950,236 A | | 8/1990 | Wilson | |
| 4,986,428 A | * | 1/1991 | Signorini .................... | 215/11.3 |
| 5,020,679 A | * | 6/1991 | Signorini .................... | 215/11.1 |
| 5,295,957 A | | 3/1994 | Aida et al. | |
| 5,358,476 A | | 10/1994 | Wilson | |
| 5,758,787 A | * | 6/1998 | Sheu .......................... | 215/11.1 |
| 5,806,711 A | | 9/1998 | Morano et al. ............... | 221/33 |
| 5,878,899 A | | 3/1999 | Manganiello et al. ...... | 215/11.6 |
| 5,894,947 A | | 4/1999 | Morano ....................... | 215/11.3 |
| 5,921,426 A | | 7/1999 | Randolph .............. | 220/495.06 |
| 5,993,479 A | | 11/1999 | Prentiss ....................... | 606/236 |
| 6,003,698 A | | 12/1999 | Morano ....................... | 215/11.1 |
| 6,050,432 A | | 4/2000 | Koehnke .................... | 215/11.3 |
| 6,210,360 B1 | | 4/2001 | Kong .......................... | 604/73 |
| 6,328,082 B1 | * | 12/2001 | Lafond ........................ | 141/313 |
| 2001/0016708 A1 | | 8/2001 | Kong et al. ................ | 604/152 |

FOREIGN PATENT DOCUMENTS

WO        9426231        * 11/1994

* cited by examiner

*Primary Examiner*—Sue A. Weaver
(74) *Attorney, Agent, or Firm*—Ohlandt, Greeley, Ruggiero & Perle, LLP

(57) ABSTRACT

A breast milk feeding and storage system is provided. The system has a liner having an open end, a holder having an open end, and an adapter system. The liner open end and the adapter system are engageable with the holder open end to allow a user to selectively insert breast milk into the liner, feed the breast milk from the liner or store the breast milk in the liner.

29 Claims, 11 Drawing Sheets

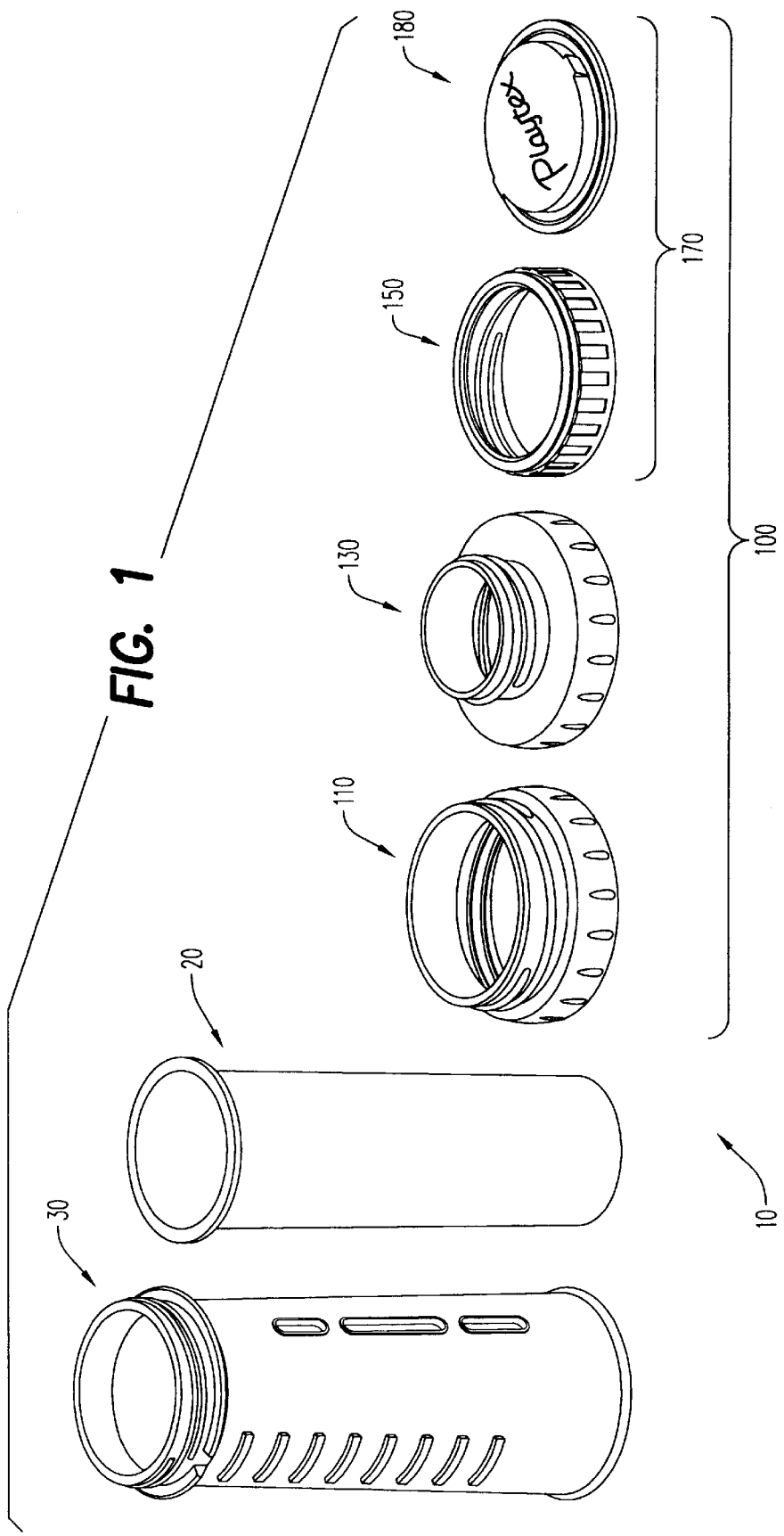

INFANT FEEDING AND STORAGE SYSTEM

BACKGROUND OF THE INVENTION

1. Field of the Invention

The present invention relates to infant feeding systems. More particularly, the present invention relates to breast milk feeding and storage systems.

2. Description of the Prior Art

Breast pumps and storage containers are known in the art. The conventional devices and methods require a user to pump breast milk into a rigid, reusable container and then pour the breast milk into a separate storage sac. The storage sac is typically sealed with a clip or twist tie and then placed in a refrigerator for storage. These devices and methods suffer from the drawback of requiring multiple containers, as well as requiring the pouring of the breast milk from one container to another container. This requires additional clean up and adds the risk that the breast milk may be wasted if it is spilled or contaminated during the process.

Additionally, the conventional devices and methods then require a user to remove the clip or twist tie from the storage sac and pour the breast milk into a feeding bottle to feed the baby. These devices and methods again suffer from the drawbacks of requiring additional cleanup, the risk of spilling the breast milk and the risk of contamination during the process.

Given the time spent and the difficulty encountered in obtaining breast milk using a breast pump, the loss of breast milk due to spillage or due to contamination, is of concern in this process. Additionally, given the health implications for an infant, the cleanliness and sterilization of the components of the system are of great concern in this process.

SUMMARY OF THE INVENTION

It is an object of the present invention to provide an infant feeding system that reduces the number of containers necessary for feeding and storage of breast milk.

It is another object of the present invention to provide an infant feeding system that reduces the risk of spillage or contamination due to the use of multiple containers.

It is yet another object of the present invention to provide an infant feeding system that reduces the amount of clean up due to the use of multiple containers.

The above objects and advantages of the present invention are provided by a breast milk feeding and storage system comprising a liner having an open end, a holder having an open end, and an adapter system. The liner open end and the adapter system are engageable with the holder open end to allow a user to selectively insert breast milk into the liner, feed the breast milk from the liner or store the breast milk in the liner. Preferably, the adapter system has a liner ring, a pump ring, a nipple ring and a storage cap. More preferably, the liner and the liner ring are engageable with the holder open end, the pump ring is engageable with the liner ring and a breast pump for inserting the breast milk into the liner, the nipple ring is engageable with the liner ring and a nipple for feeding the breast milk from the liner, and the storage cap is engageable with the liner ring for storing the breast milk. Most preferably, the holder open end, liner ring, pump ring, nipple ring and storage cap are threadingly engageable.

BRIEF DESCRIPTION OF THE DRAWINGS

Other and further objects, advantages and features of the present invention will be understood by reference to the following:

FIG. 1 is an exploded view of the components of the breast milk feeding and storage system of the present invention;

DESCRIPTION OF THE INVENTION

Figure 3:
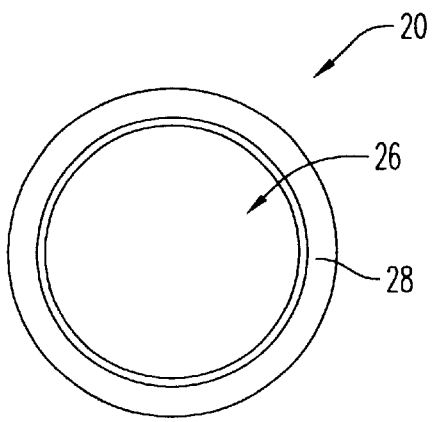
FIG. 3 is a top view of the liner of FIG. 2.

Referring to FIG. 1, there is shown the preferred embodiment of the components of the breast milk feeding and storage system of the present invention generally represented by reference numeral 10. System 10 has a liner 20, a holder 30 and an adapter system 100. Adapter system 100 preferably has a liner ring 110, a pump ring 130, a nipple ring 150 and a storage cap 170.

Figure 2:
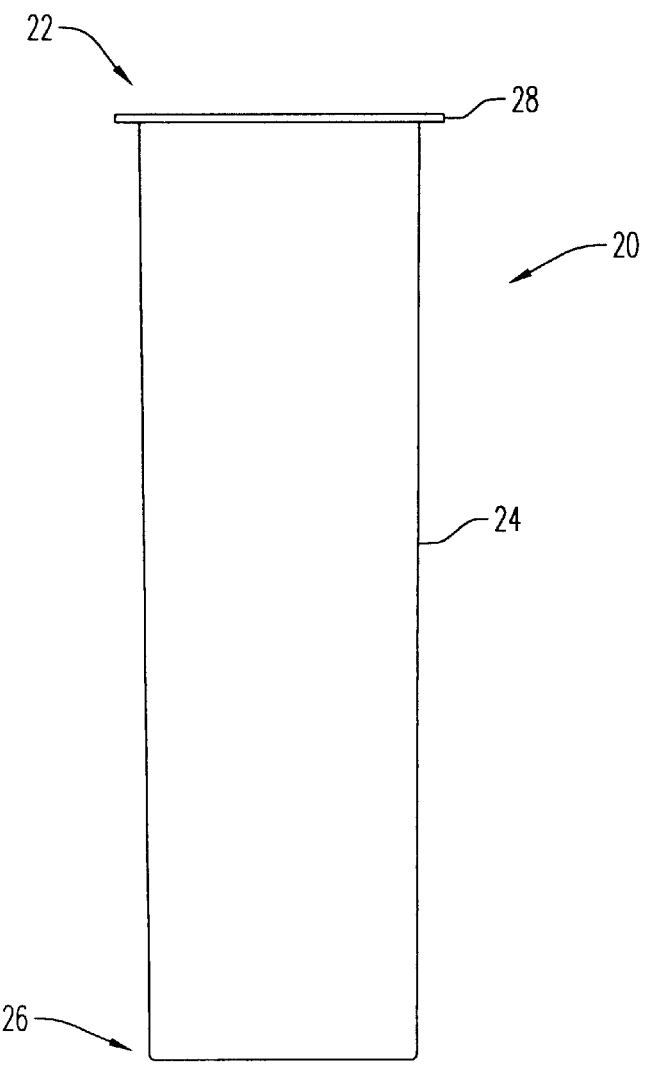
FIG. 2 is a plan view of the liner of FIG. 1.

Referring to FIG. 2, in the preferred embodiment, liner 20 is substantially cylindrical in shape, having an open end 22, a liner body 24 and a closed end 26. Liner 20 is preferably tapered toward closed end 26 to allow stacking of multiple liners 20 upon each other for facilitating storage. More preferably, liner 20 is tapered up to about 2.0 degrees. Liner body 24 and closed end 26 define a volume for holding the breast milk. Preferably, liner body 24 has a height of about 5.25 inches to about 6.50 inches. Closed end 26 is preferably circular in shape. More preferably, closed end 26 has an outer circumference of about 4.710 inches to about 5.966 inches.

Referring to FIGS. 2 and 3, liner open end 22 is preferably circular in shape. More preferably, open end 22 has an inner circumference of about 5.574 inches to about 6.594 inches. Open end 22 is adapted for engagement with adapter system 100. In the preferred embodiment, open end 22 has a resilient flange 28 extending outwardly from liner body 24. Preferably, flange 28 extends along the entire circumference of liner body 24. More preferably, flange 28 is substantially perpendicular to liner body 24. Flange 28 preferably has an outer circumference of about 5.966 inches to about 7.065 inches. Flange 28 engages with liner ring 110, which will be discussed later in detail.

In the preferred embodiment, flange 28 is integrally formed with liner body 24. Preferably, flange 28 is made from the same material as liner body 24. However, flange 28 is thicker, and thus harder and more resilient than liner body 24. Flange 28 needs to be flexible enough to dispense from a dispensing package and at the same time, rigid enough to support the weight of the breast milk contained therein when engaged with liner ring 110, so as not to slide through liner ring 110. This is achieved through a combination of flange thickness and material selection. Any type of flexible material, or combination of material can be selected to construct liner 20. Preferably, liner 20 is made from polyethylene resin. More preferably, liner 20 is made from a low density polyethylene resin, and most preferably liner 20 is made from a linear low density polyethylene resin. An example of liner 20 is shown in U.S. Pat. No. 5,806,711 assigned to Playtex Products, Inc, the disclosures of which are incorporated herein by reference.

Figure 4:
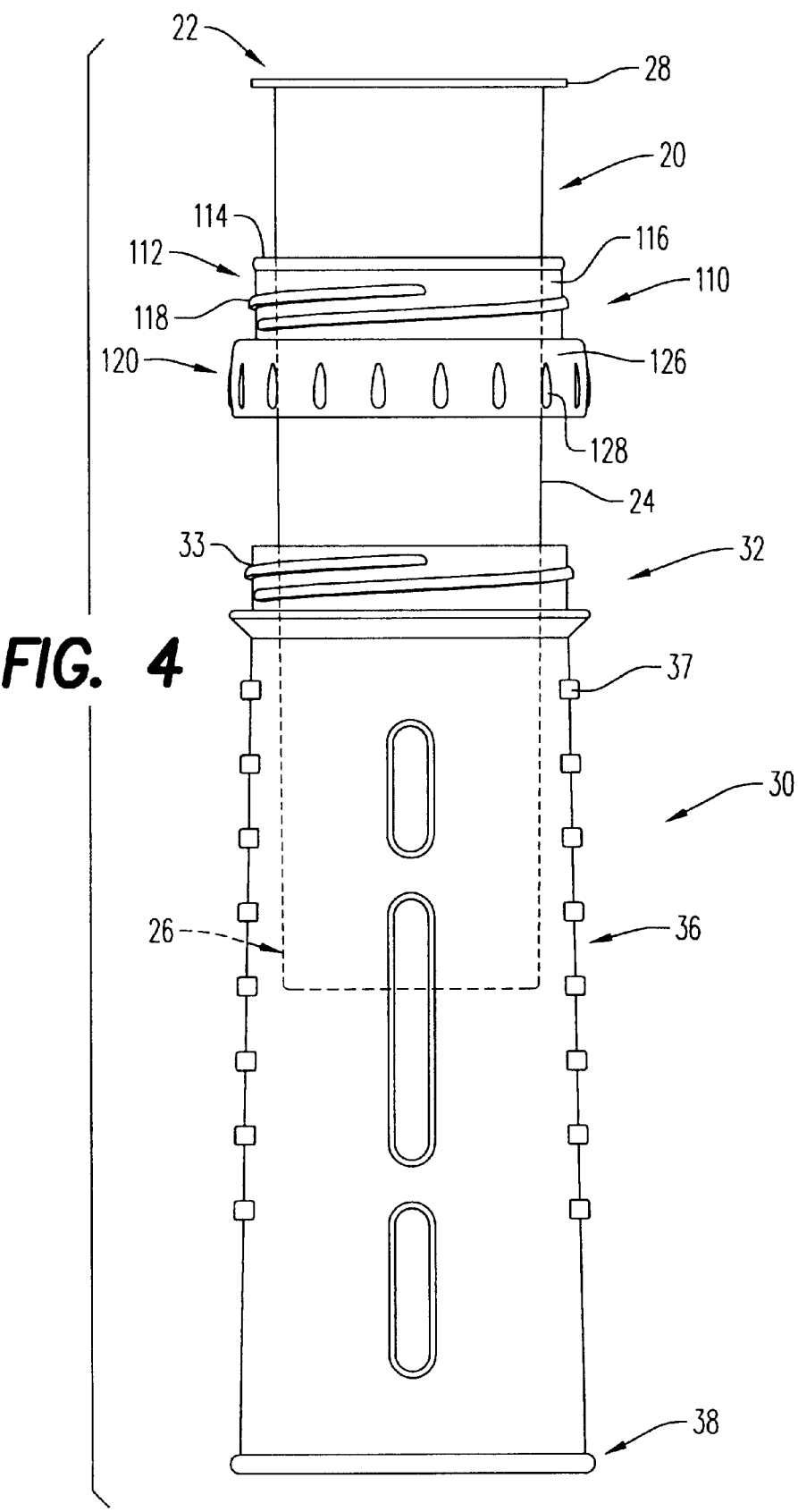
FIG. 4 is an exploded plan view of the liner, liner ring and holder of FIG. 1.

Referring to FIG. 4, while the preferred embodiment has a liner 20 that is substantially cylindrical in shape with a flange 28 for engagement with adapter system 100 (liner ring 110 in this preferred embodiment), it should be apparent to one skilled in the art that liner 20 can assume other shapes and can also be alternatively adapted to achieve engagement with adapter system 100, such as having flexible tabs formed at liner open end 22. Also, while the preferred embodiment has a disposable liner 20 for holding the breast milk, other containers, including reusable, rigid containers can be used with adapter system 100 in order to selectively insert breast milk into the container, feed the breast milk from the container or store the breast milk in the container. One advantage of the present invention is that system 10 utilizes a single container, i.e., liner 20, for pumping, feeding and storing of the breast milk. This reduces clean up, as well as the risk of wasting breast milk through spillage or contamination. A further advantage of the preferred embodiment of the present invention results from the use of a container, i.e., liner 20, that is disposable. This further reduces the amount of clean up necessary since after liner 20 is used for pumping, feeding and storage of the breast milk, it can be discarded and a new liner 20 can be used with system 10. The clean up is thus limited to the other components of system 10.

Holder 30 is substantially cylindrical in shape, having a top end 32, a holder body 36 and a bottom end 38. Top end 32 is open and is preferably circular in shape. Top end 32 has an inner circumference that is large enough to receive liner body 24. Holder body 36 has an inner circumference and volume that is large enough to receive liner body 24. In the preferred embodiment, bottom end 38 is open which facilitates cleaning of holder 30, reduces the amount of material and simplifies production. Thus, in the preferred embodiment, open top end 32, holder body 36 and open bottom end 38 form a uniform sleeve for housing liner 20. However, alternative shapes and sizes of holder 30 can be used to hold liner 20, such as widening bottom end 38 for added stability to holder 30.

In the preferred embodiment, holder top end 32 has external threads 33 formed thereon. Threads 33 allow engagement of holder top end 32 with liner ring 110, which will be discussed later in detail. However, top end 32 can be alternatively adapted to allow engagement of holder 30 with liner ring 110, such as an annular ring formed in top end 32 for a snap fit with liner ring 110.

Preferably, holder body 36 has a series of ridges 37 formed thereon. More preferably, ridges 37 are integrally formed with holder body 36. Ridges 37 form a gripping surface to allow a user to readily grip holder 30 in one hand. This is especially significant when the user is pumping breast milk into liner 20, which may require use of the user's other hand. Preferably, ridges 37 are horizontally positioned, and are of small extent. The space between ridges 37 can receive the user's fingers. Alternatively, holder body 36 have other gripping structures, such as one or more embossments, slots, or the like.

Holder 30 can be made of any material that will not warp and is capable of holding liner 20 when filled with breast milk. Preferably, holder 30 is made of a rigid molded material, such as a rigid thermoplastic. More preferably, holder 30 is made of polypropylene.

Referring to FIG. 1, in the preferred embodiment, adapter system 100 has a liner ring 110, a pump ring 130, a nipple ring 150 and a storage cap 170, which allow a user to selectively insert breast milk into liner 20, feed the breast milk from liner 20 or store the breast milk in liner 20.

Figure 6:
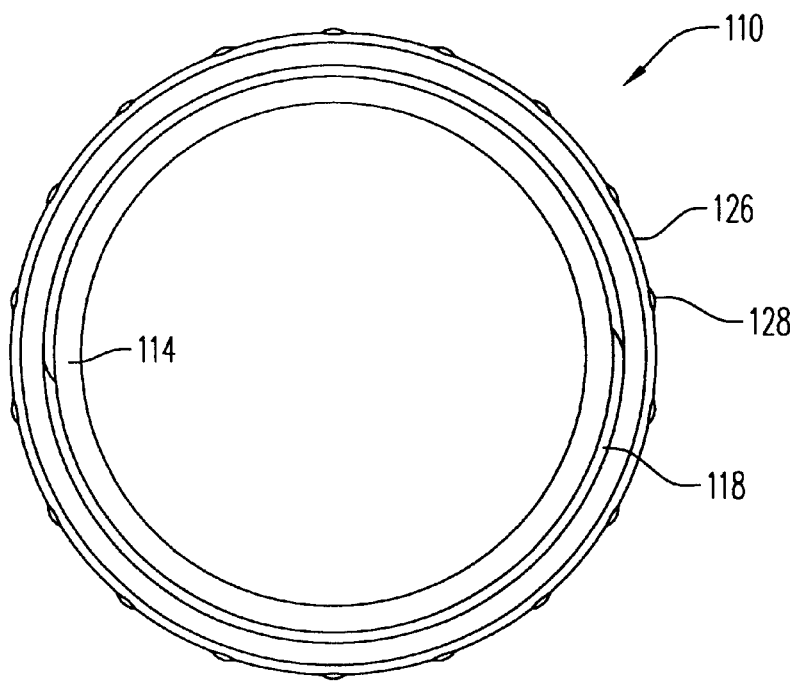
FIG. 6 is a top view of the liner ring of FIG. 1.
Figure 5:
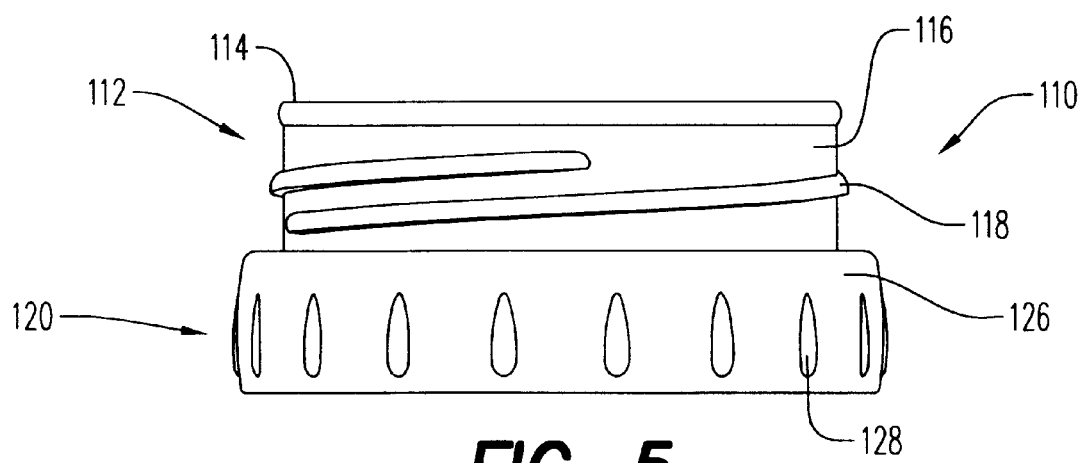
FIG. 5 is a plan view of the liner ring of FIG. 1.
Figure 7:
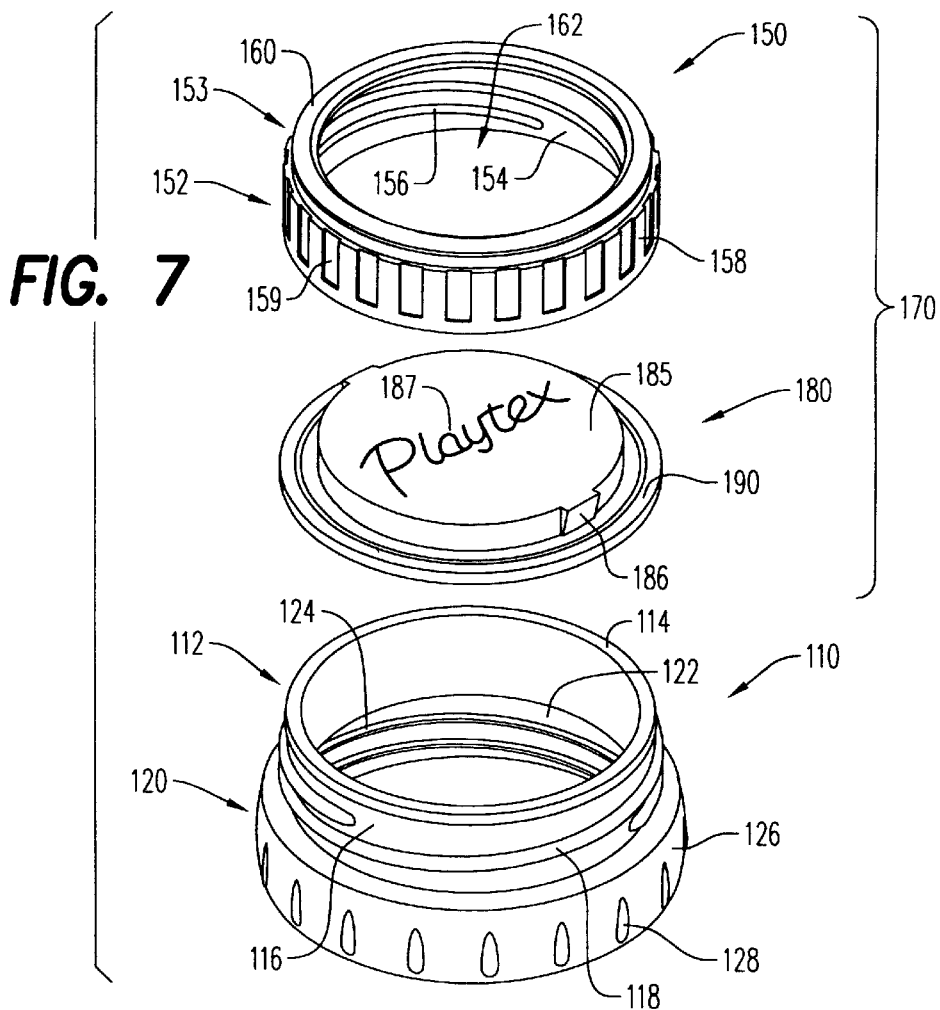
FIG. 7 is an exploded perspective view of the liner ring, nipple ring and storage cap of FIG. 1.

Referring to FIGS. 5 through 7, liner ring 110 is substantially cylindrical in shape, having an upper portion 112 with a first inner circumference and a lower portion 120 with a second inner circumference. Upper portion 112 and lower portion 120 form a sleeve with two integral sections that allow housing and engagement of liner 20 and liner flange 28.

Lower portion 120 has an inner surface 122 with inner threads 124 formed thereon. The inner circumference of lower portion 120 is slightly larger than the outer circumference of holder top end 32 so that inner threads 124 threadingly engage with holder external threads 33. Thus, lower portion 120 acts as a retaining ring so that liner ring 110 can be threadingly engaged to holder 30. In the preferred embodiment, liner ring 110 and holder 30 threadingly engage. However, if holder 30 is adapted for an alternative type of engagement, then lower portion 120 will also be adapted for the corresponding type of alternative engagement, such as an annular ring and annular groove that provide a snap-fit engagement.

Lower portion 120 further has an outer surface 126 with ribs 128 formed thereon. Preferably, ribs 128 are integrally formed with liner ring 110. Ribs 128 form a gripping surface to allow a user to readily grip liner ring 110 for engaging and disengaging with holder 30. Preferably, ribs 128 are vertically positioned, and are of small extent. The space between ribs 128 can receive the user's fingers. Alternatively, liner ring 110 can be made with other gripping structures, such as embossments, slots, or the like.

Upper portion 112 has a rim 114 for seating liner flange 28. The inner circumference of upper portion 112 is larger than the outer circumference of liner body 24 but less than the outer circumference of liner flange 28. This allows liner body 24 to pass through liner ring 110 but prevents liner flange 28 from doing so. Thus, liner flange 28 sits upon rim 114 of liner ring 110, and liner 20 and liner ring 110 are engaged.

Upper portion 112 further has an outer surface 116 having external liner threads 118 formed thereon. Liner threads 118 allow engagement of liner ring 110 with pump ring 130 or nipple ring 150, which will be discussed later in detail. However, upper portion 112 can be alternatively allowed to engage liner ring 110 with pump ring 130 or nipple ring 150, such as an annular ring formed in upper portion 112 providing for a snap-fit engagement with pump ring 130 or nipple ring 150.

Liner ring 110 is preferably formed from a sturdy material such as a rigid polypropylene. More preferably, the material is opaque to block any view of inner threads 124 or other alternative engagement structure on liner ring 110.

Figure 8:
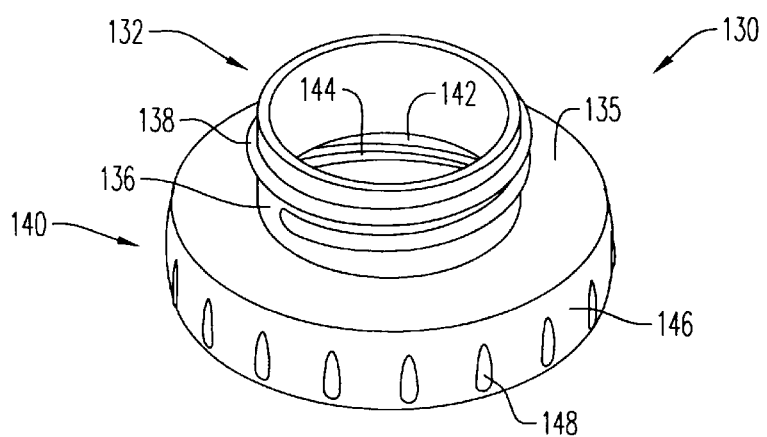
FIG. 8 is a perspective view of the pump ring of FIG. 1.
Figure 9:
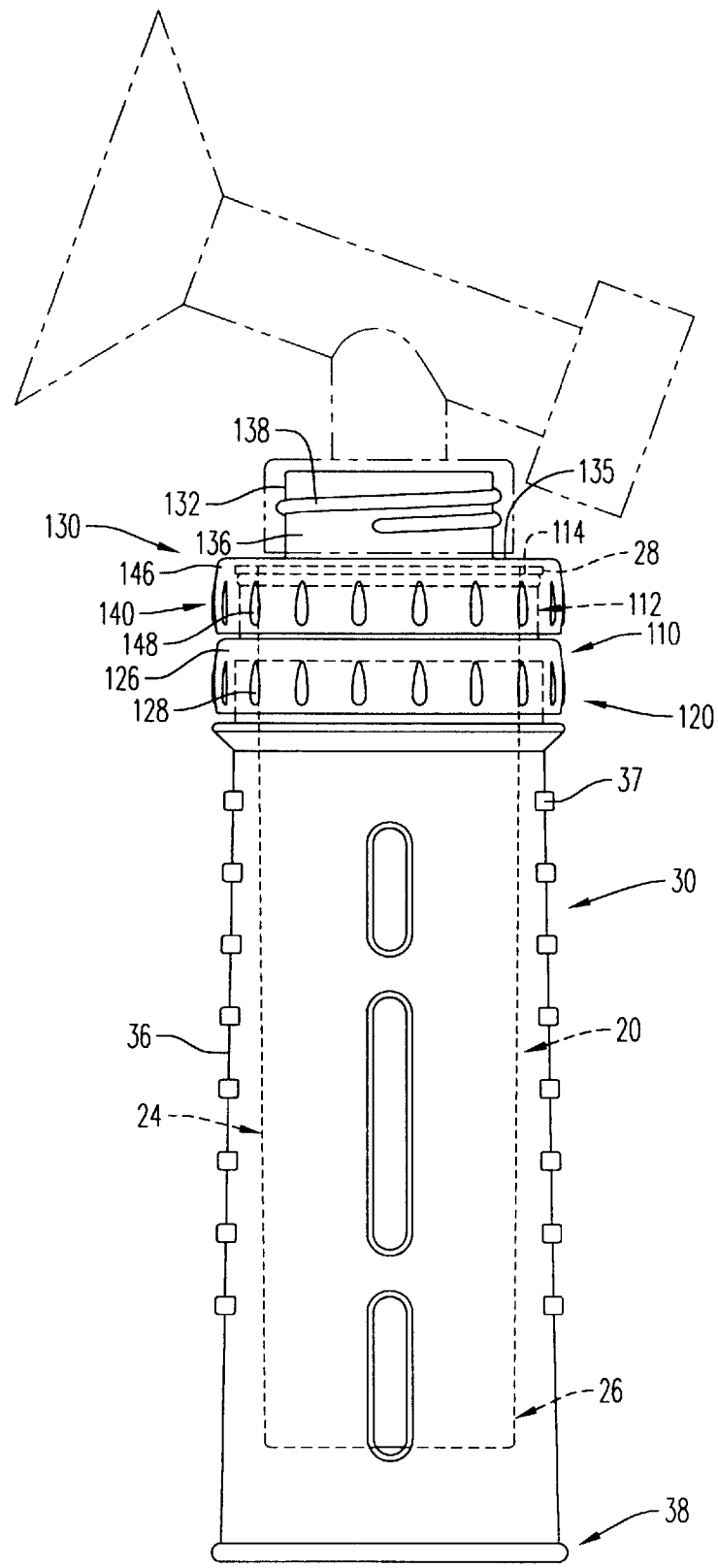
FIG. 9 is a plan view of the liner, holder, liner ring and pump ring of FIG. 1, engaged with a breast pump.
Figure 13:
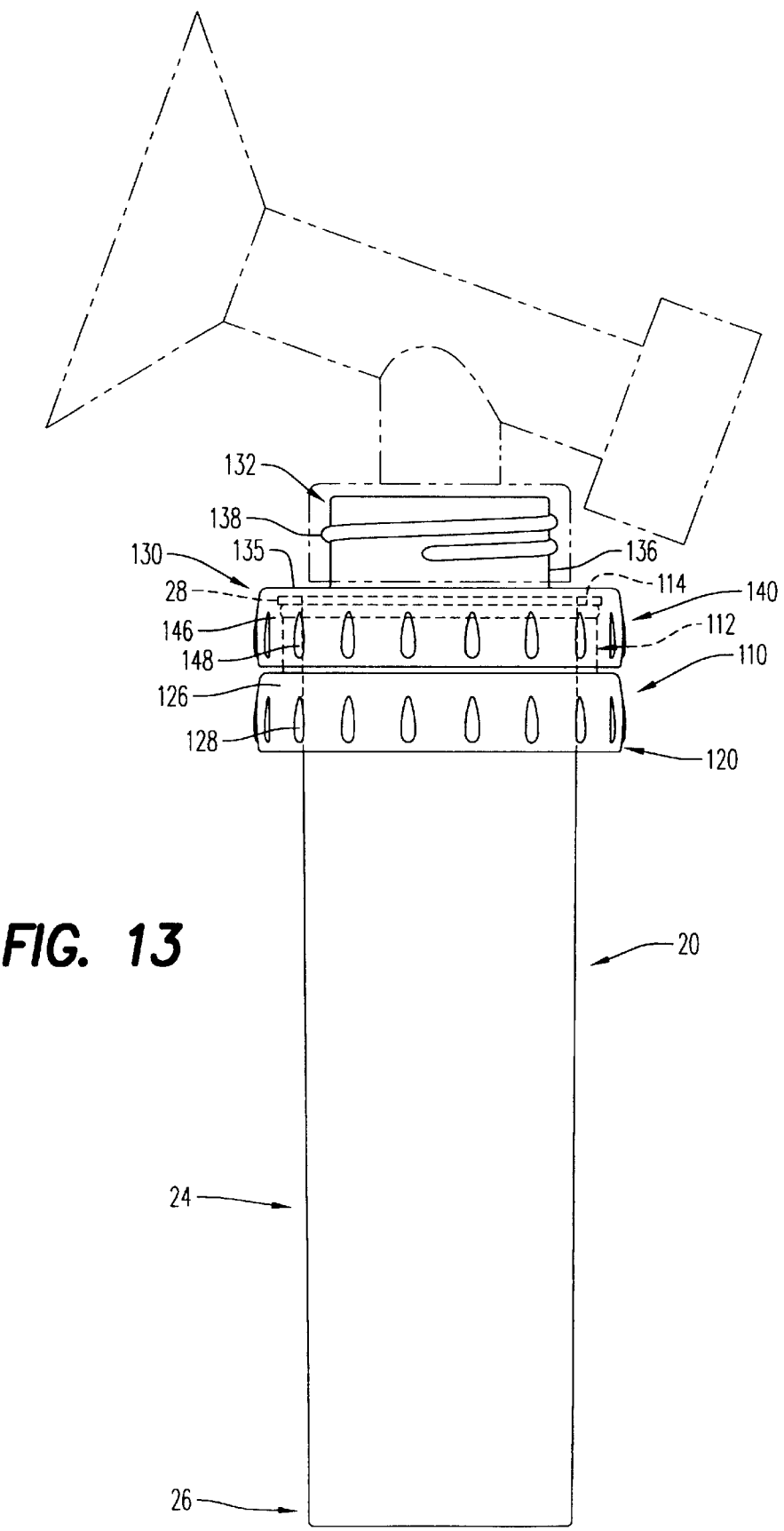
FIG. 13 is a plan view of the liner, liner ring and pump ring of FIG. 1, engaged with a breast pump.

Referring to FIGS. 8, 9 and 13, pump ring 130 is substantially cylindrical in shape, having an upper section 132 and a lower section 140 connected by a center section 135. Upper section 132 and lower section 140 form a cylindrical channel with two integral portions, allowing engagement of a breast pump, and through which breast milk is inserted into liner 20.

Lower section 140 has an inner surface 142 with inner threads 144 formed thereon. The inner circumference of lower section 140 is slightly larger than the outer circumference of upper portion 112 of liner ring 110 so that inner threads 144 threadingly engage with liner threads 118. Thus, lower section 140 acts as a retaining ring so that pump ring 130 can be threadingly engaged to liner ring 110. In the preferred embodiment, pump ring 130 and liner ring 110 threadingly engage. However, if liner ring 110 is adapted for an alternative type of engagement, then lower section 140 will also be adapted for the corresponding type of alternative engagement such as an annular ring and annular groove, providing a snap-fit engagement.

Lower section 140 further has an outer surface 146 with ribs 148 formed thereon. Preferably, ribs 148 are integrally formed with pump ring 140. Ribs 148 form a gripping surface to allow a user to readily grip pump ring 130 for engaging and disengaging with liner ring 110. Preferably, ribs 148 are vertically positioned, and are of small extent. The space between ribs 148 can receive the user's fingers. Alternatively, pump ring 130 can be adapted with other gripping structures, such as embossments, slots, or the like.

Center section 135 is substantially horizontal and extends inwardly from inner surface 142 to upper section 132. Upper section 132 has an outer surface 136 having external pump threads 138 formed thereon. The circumference of outer surface 136 allows pump threads 138 to engage standard breast pumps having internal threads. However, upper section 132 can be alternatively adapted to allow engagement of pump ring 130 with a breast pump having another type of engagement structure.

Pump ring 130 is preferably formed from a sturdy material such as a rigid polypropylene. More preferably, the material is opaque to block any view of inner threads 144 or other alternative engagement structures on pump ring 130.

Engagement of pump ring 130 with liner ring 110 causes a compressive force to be exerted upon liner flange 28 that is seated between center section 135 and rim 114 of liner ring 110. Thus, liner 20 is sealingly engaged with a breast pump for inserting breast milk therein.

Figure 10:
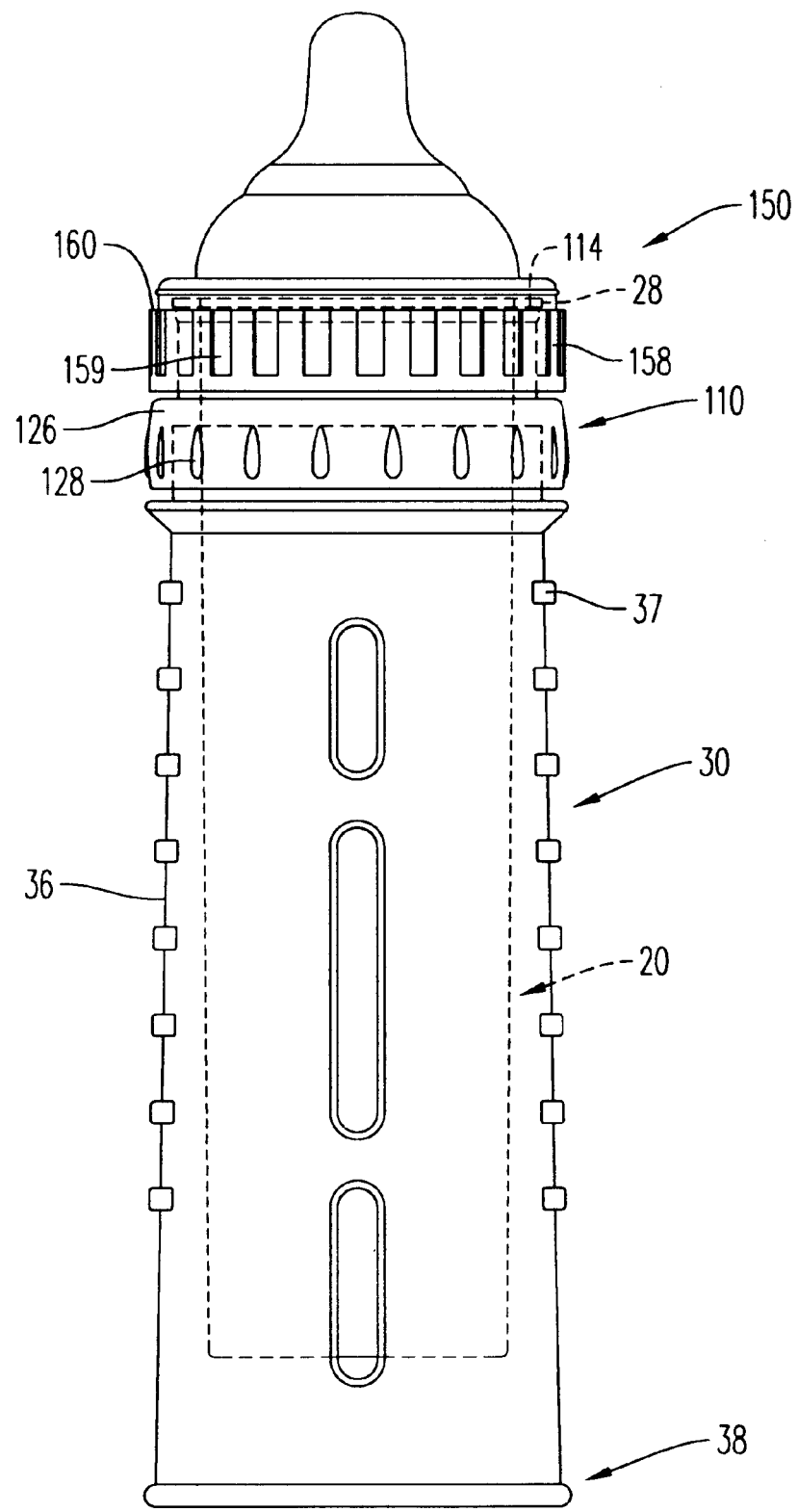
FIG. 10 is a plan view of the liner, holder, liner ring and nipple ring of FIG. 1, engaged with a nipple.

Referring to FIGS. 7 and 10, nipple ring 150 is substantially cylindrical in shape or a curved annular structure that is adapted to engage liner ring 110. Nipple ring 150 has a circumferential or annular sleeve 152 having a top region 153 and an edge or rim 160. Sleeve 152 has an inner surface 154 having inner threads 156 formed thereon. The circumference of inner surface 154 is slightly larger than the circumference of outer surface 116 of liner ring 110 allowing inner threads 156 to threadingly engage with liner threads 118. Thus, sleeve 152 acts as a retaining ring so that nipple ring 150 can be threadingly engaged to liner ring 110. In the preferred embodiment, nipple ring 150 and liner ring 110 threadingly engage. However, if liner ring 110 is adapted for an alternative type of engagement, then sleeve 152 will also be adapted for the corresponding type of alternative engagement such as an annular ring and annular groove, providing for a snap-fit engagement.

Sleeve 152 further has an outer surface 158 having a series of apertures 159 formed therein. Apertures 159 form a gripping surface to allow a user to readily grip nipple ring 150 for engaging and disengaging with liner ring 110. Preferably, apertures 159 are vertically positioned. Alternatively, nipple ring 150 can have other gripping structures, such as indentations, slots or the like.

In the preferred embodiment, top region 153 has nipple ring edge 160 extending inwardly from sleeve 152 defining a nipple opening 162. Preferably, edge 160 extends along the entire circumference of sleeve 152. More preferably, edge 160 is substantially perpendicular to sleeve 152. Edge 160 is preferably integrally formed with sleeve 152. A standard nipple having a base with a flange extending outwardly therefrom, can be passed through nipple opening 162 where edge 160 engages with the nipple flange.

Nipple ring 150 is preferably formed from a sturdy material such as a rigid polypropylene. More preferably, the material is opaque to block any view of inner threads 156 or other alternative engagement structure on nipple ring 150.

Engagement of nipple ring 150 with liner ring 110 causes a compressive force to be exerted upon the base flange of the nipple and liner flange 28, which are seated upon each other and between nipple edge 160 and rim 114 of liner ring 110. Thus, liner 20 is sealingly engaged with a nipple for breastfeeding an infant.

In this embodiment, a nipple ring 150 having a nipple opening 162 for engagement with a separate nipple is used. However, alternative types of nipple rings can also be used, such as a one-piece nipple and retainer ring that would engage with liner ring 110.

Figure 11:
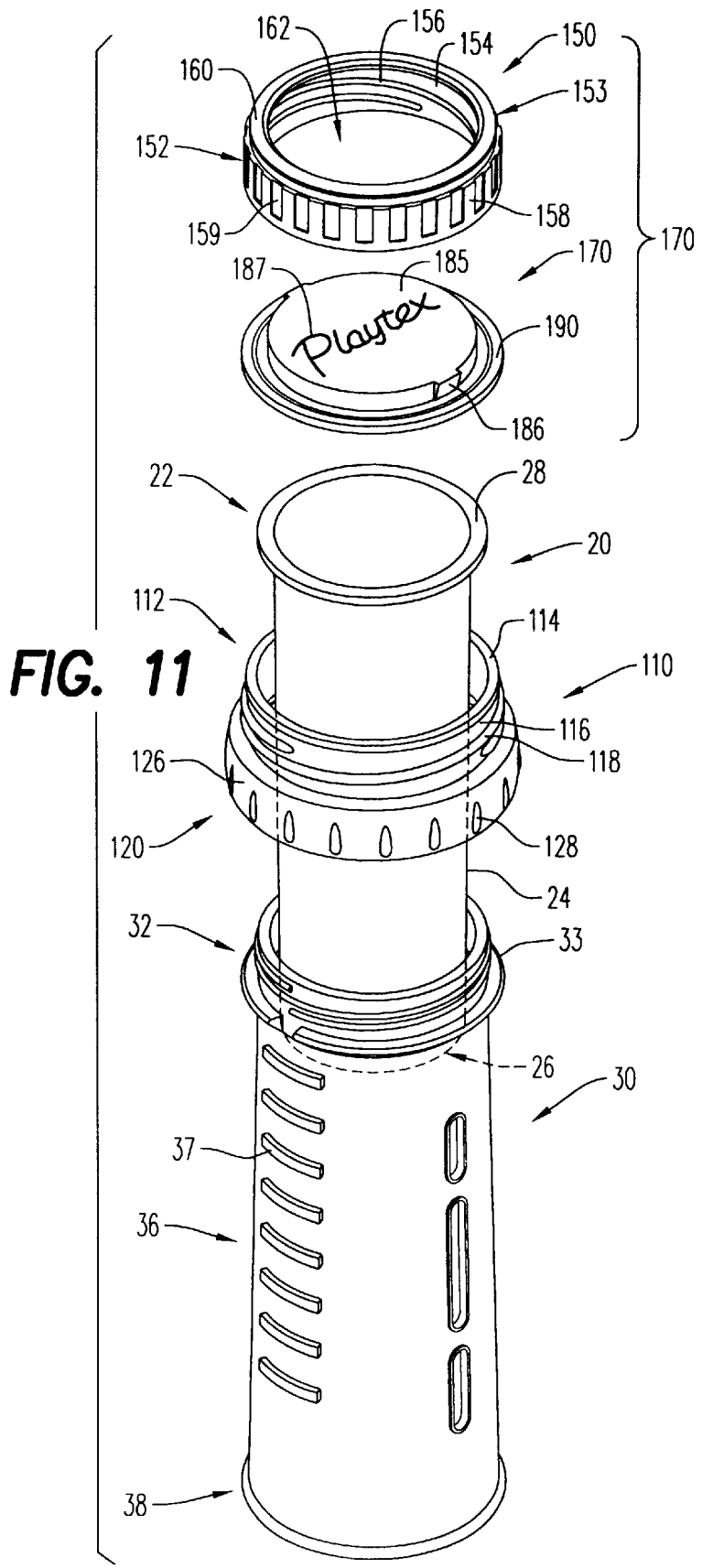
FIG. 11 is an exploded plan view of the liner, holder, liner ring, sealing disc and nipple ring of FIG. 1.
Figure 12:
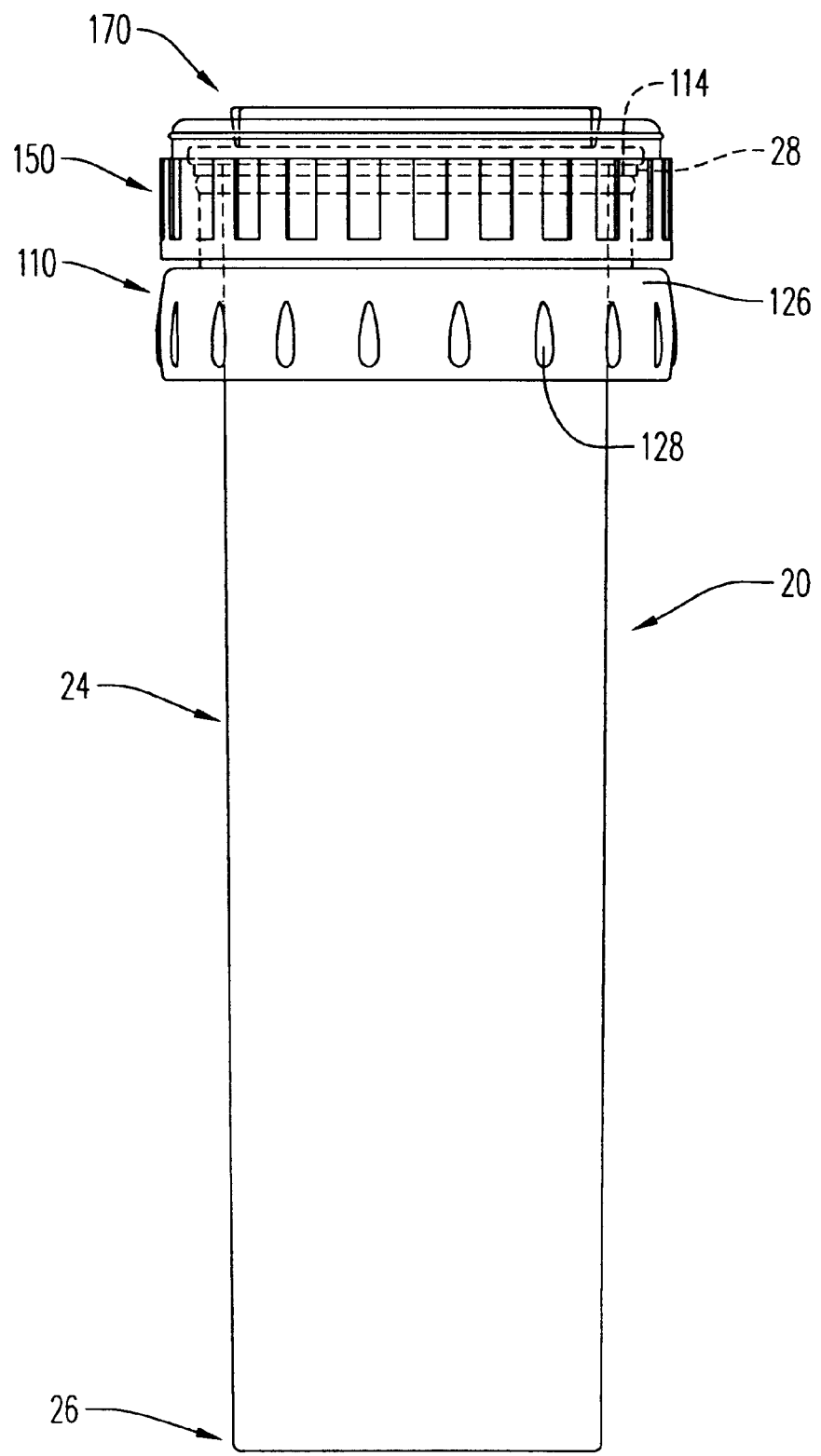
FIG. 12 is a plan view of the liner, liner ring, nipple ring and sealing disc of FIG. 1.

Referring to FIGS. 7, 11 and 12, in the preferred embodiment, storage cap 170 has a sealing disc 180 that can engage with nipple ring 150. This allows a user to easily switch between the storage function and the feeding function of system 10, which both utilize nipple ring 150, as well as reducing the amount of material required for manufacture. However, storage cap 170 can also be a separate, one-piece unit that is engageable with liner ring 110.

Sealing disc 180 has a disc-like shape with a bottom flange 190. Bottom flange 190 extends outwardly from disc 180. Preferably, flange 190 extends along the entire circumference of disc 180. More preferably, flange 190 is substantially perpendicular to disc 180. Flange 190 is preferably integrally formed with disc 180. The outer circumference of flange 190 is larger than the inner circumference of nipple ring edge 160. The outer circumference of disc 180 is slightly smaller than the inner circumference of nipple ring edge 160. This allows disc 180 to pass through nipple opening 162 up to flange 190. The small difference in circumferences between nipple ring edge 160 and sealing disc 180 provides a sealing engagement of sealing disc 180 with nipple ring 150. Preferably, sealing disc 180 also has a pair of tabs 186. Tabs 186 protrude from the side of disc 180, allowing a user to temporarily hold the disc in place in nipple ring 150. Preferably, tabs 186 are oppositely positioned along disc 180 and have a decreasing width toward flange 190. This decreasing width facilitates connection of disc 180 to nipple ring 150.

Sealing disc 180 is preferably formed from a flexible material such as a thermoplastic elastomer. In this embodiment, sealing disc 180 further has a top surface 185 having letters 187 imprinted therein. This is useful to the user or consumer in identifying the particular product that is being used or purchased.

Engagement of nipple ring 150 with liner ring 110 causes a compressive force to be exerted upon disc flange 190 and liner flange 28, which are seated upon each other and between nipple edge 160 and rim 114 of liner ring 110. Thus, liner 20 is sealingly engaged with storage cap 170 for storage of the breast milk.

Figure 14:
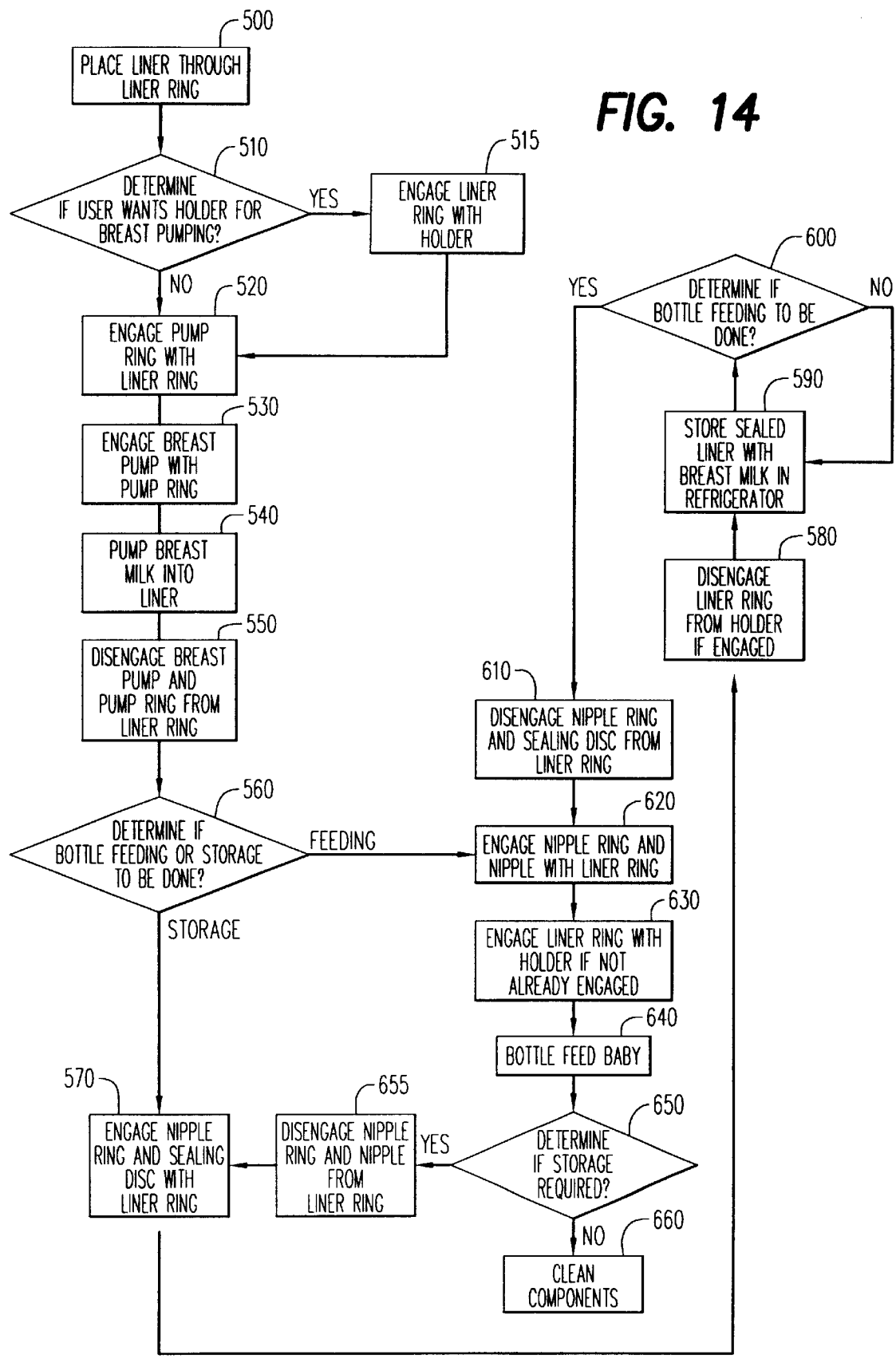
FIG. 14 is a flowchart of the method for using the breast milk feeding and storage system of the present invention.

Referring to FIG. 14, the following steps can be taken for pumping, feeding and storage of breast milk according to system 10 of the present invention. In step 500, the user places liner 20 through rim 114 of liner ring 110. This causes flange 28 to sit upon rim 114. The user then determines if she wants to use holder 30 while breast pumping (step 510). If the user wants to use holder 30, then she engages inner threads 124 of liner ring 110 with holder threads 33, as in step 515. The user then engages pump ring 130 with liner ring 110 by engaging inner threads 144 of pump ring 130 with liner threads 118 of liner ring 110 (step 520). In step 530, the user engages a breast pump with pump ring 130 by engaging pump threads 138 of pump ring 130 with the internal threads of a breast pump. Pump threads 138 have a circumference that engages with standard breast pumps having internal threads located on the breast pump. The user can now begin the process of using the breast pump to obtain breast milk (step 540). The breast milk passes through pump ring 130 and liner ring 110, and into liner 20. Due to the sealing engagement of liner 20 with liner ring 110, pump ring 130 and the breast pump, system 10 alleviates the risk of spillage of breast milk during the breast pumping process.

Once the breast pumping process is finished, the user can utilize system 10 to either bottle-feed the infant or store the breast milk. In step 550, the user disengages the breast pump and pump ring 130 from liner ring 110. The user then determines whether bottle-feeding or storage of the breast milk is to be done, as in step 560.

If the breast milk is to be stored for later feeding of the infant, then the user engages nipple ring 150 and sealing disc 180 with liner ring 110 (step 570). Sealing disc 180 is positioned inside of nipple sleeve 152 so that top surface 185 of the sealing disc passes through nipple opening 162 and bottom flange 190 of the sealing disc sealingly engages the underside of nipple ring edge 160. Inner threads 156 of nipple ring 150 are then engaged with liner threads 118 of liner ring 110. This causes a sealing engagement between the underside of bottom flange 190 of sealing disc 180 and the top surface of liner flange 28. The user then disengages liner ring 110 from holder 30, if the holder was used during the breast pumping process (step 580). The breast milk can then be stored in the refrigerator, as in step 590.

System 10 allows the user to pump the breast milk into liner 20 and then seal the liner for storage until feeding the infant at a later time. The use of multiple containers is avoided. Thus, the cleanup and sterilization of the components of system 10 is simplified, as compared to the conventional devices. Also, the user is not required to pour the breast milk from one container to another container, as required by the conventional devices. Thus, the loss of breast milk either through spillage or contamination is also prevented.

In step 600, the user determines if bottle-feeding of the infant is to be done. If the infant requires feeding, the user disengages nipple ring 150 and sealing disc 180 from liner ring 110, as in step 610. In step 620, the user engages nipple ring 150 and a nipple with liner ring 110. The nipple is positioned in nipple ring 150 so that the stem and bulbous area of the nipple passes through nipple opening 162 and the top surface of the outer flange of the nipple sealingly engages the underside of nipple ring edge 160. Inner threads 156 of nipple ring 150 are then engaged with liner threads 118 of liner ring 110. This causes a sealing engagement between the underside of the base flange of the nipple and the top surface of liner flange 28.

In step 630, the user engages liner ring 110 with holder 30 (if not already engaged during the breast pumping process). The infant can now be bottle fed with the breast milk, as in step 640.

Once the bottle-feeding is finished, the user determines if there is any breast milk remaining that requires storage (step 650). If there is breast milk remaining, the user disengages nipple ring 150 and the nipple from liner ring 110, as in step 655. The user repeats the storage process, as described in steps 570 through 600.

If there is no breast milk remaining after the infant is bottle fed, then the user can clean and sterilize the components of system 10, as in step 660. System 10 uses a single container, i.e., liner 20, to hold the breast milk during pumping, storage and feeding. This minimizes the clean up and sterilization that the user must perform, as compared to the conventional devices. Also, in the preferred embodiment, liner 20 is a disposable liner. Thus, the user's clean up is further reduced by requiring clean up and sterilization of only the remaining components of system 10 which are liner ring 110, pump ring 130, nipple ring 150, sealing disc 180, the breast pump and the nipple.

The present invention having been thus described with particular reference to the preferred forms thereof, it will be obvious that various changes and modifications may be made therein without departing from the spirit and scope of the present invention as defined in the appended claims.

What is claimed is:

1. A breast milk feeding and storage system comprising a liner having a liner open end, a holder having an open end, and an adapter system,
   wherein said liner open end and said adapter system are engageable with said holder open end to allow a user to selectively insert breast milk into said liner, feed said breast milk from said liner or store said breast milk in said liner,
   wherein said adapter system has a liner ring, a pump ring, a nipple ring and a storage cap,
   wherein said liner and said liner ring are engageable with said open end of said holder, said pump ring is engageable with said liner ring and a breast pump for inserting said breast milk into said liner, said nipple ring is engageable with said liner ring and a nipple for feeding said breast milk from said liner, and said storage cap is engageable with said liner ring for storing said breast milk, and
   wherein said storage cap includes a storage disc that is sealingly engageable with said nipple ring and said liner open end.

2. The breast milk feeding and storage system of claim 1, wherein said open end of said liner has a flange extending therefrom for engagement with said adapter system.

3. The breast milk feeding and storage system of claim 1, wherein said liner ring is threadingly engageable with said open end of said holder.

4. The breast milk feeding and storage system of claim 1, wherein said pump ring is threadingly engageable with said liner ring.

5. The breast milk feeding and storage system of claim 1, wherein said nipple ring is threadingly engageable with said liner ring.

6. The breast milk feeding and storage system of claim 1, wherein said breast pump is threadingly engageable with said pump ring.

7. The breast milk feeding and storage system of claim 1, wherein said open end of said holder has external threads formed therein for engagement with said liner ring.

8. The breast milk feeding and storage system of claim 7, wherein said liner ring comprises an upper portion and a lower portion, said upper portion having external threads formed therein for engagement with said pump ring or said nipple ring, and said lower portion having internal threads formed therein for engagement with said open end of said holder.

9. The breast milk feeding and storage system of claim 8, wherein said pump ring comprises a top portion and a bottom portion, said top portion having external threads formed therein for engagement with said breast pump and said bottom portion having internal threads formed therein for engagement with said liner ring.

10. The breast milk feeding and storage system of claim 1, wherein said nipple ring has internal threads formed therein for engagement with said liner ring.

11. A breast milk feeding and storage system comprising a liner having an open end and an adapter system,
wherein said open end of said liner and said adapter system are engageable to allow a user to selectively insert breast milk into said liner, feed said breast milk from said liner or store said breast milk in said liner,
wherein said adapter system includes a liner ring, a pump ring, a nipple ring and a storage cap,
wherein said open end of said liner is engageable with said liner ring, said pump ring is engageable with said liner ring and a breast pump for inserting said breast milk into said liner, said nipple ring is engageable with said liner ring and a nipple for feeding said breast milk from said liner, and said storage cap is engageable with said liner ring for storing said breast milk, and
wherein said nipple ring is threadingly engageable with said liner ring.

12. The breast milk feeding and storing system of claim 11, wherein said liner open end has a flange extending therefrom for engagement with said adapter system.

13. The breast milk feeding and storage system of claim 11, wherein said storage cap comprises a storage disc that is sealingly engageable with said nipple ring and said liner open end.

14. The breast milk feeding and storage system of claim 11, wherein said pump ring is threadingly engageable with said liner ring.

15. The breast milk feeding and storage system of claim 14, wherein said liner ring comprises an upper portion and a lower portion, said upper portion having external threads formed therein for engagement with said pump ring or said nipple ring.

16. The breast milk feeding and storage system of claim 14, wherein said pump ring comprises an upper portion and a lower portion, said upper portion having external threads formed therein for engagement with said breast pump and said lower portion having internal threads formed therein for engagement with said liner ring.

17. The breast milk feeding and storage system of claim 11, wherein said breast pump is threadingly engageable with said pump ring.

18. The breast milk feeding and storage system of claim 11, wherein said nipple ring has internal threads formed therein for engagement with said liner ring.

19. A breast milk feeding and storage system that collects breast milk from a breast pump, stores the breast milk and feeds the breast milk through a nipple, the system comprising:
a flexible liner;
a storage cap removably engageable with said flexible liner;
an adapter system including a breast pump ring and a nipple ring; and
a holder that supports said flexible liner,
wherein said breast pump ring removably engages said breast pump with said flexible liner and said holder, and
wherein said nipple ring removably engages said nipple with said flexible liner and said holder.

20. The system of claim 19, wherein said flexible liner has a substantially cylindrical shape with an open end, wherein said holder has a substantially cylindrical shape with first and second open ends thereby forming a sleeve, and wherein said flexible liner is at least partially disposed in said holder.

21. The system of claim 19, wherein said breast pump ring and said nipple ring have internal threads.

22. The system of claim 19, wherein said breast pump ring has external threads.

23. A breast milk feeding and storage system that collects breast milk from a breast pump, stores the breast milk and feeds the breast milk, the system comprising:
a flexible liner;
a nipple;
a storage cap removably engageable with said flexible liner;
an adapter system comprising a breast pump ring and a nipple ring; and
a holder that supports said flexible liner, wherein
said breast pump ring removably engages said breast pump with said flexible liner and said holder, and
wherein said nipple ring removably engages said nipple with said flexible liner and said holder.

24. The system of claim 23, wherein said flexible liner has a substantially cylindrical shape with an open end, wherein said holder has a substantially cylindrical shape with first and second open ends thereby forming a sleeve, and wherein said flexible liner is at least partially disposed in said holder.

25. The system of claim 23, wherein said breast pump ring and said nipple ring have internal threads.

26. The system of claim 23, wherein said breast pump ring has external threads.

27. A breast milk feeding and storage system that collects breast milk from a breast pump, stores the breast milk and feeds the breast milk, the system comprising:
a liner;
a holder;
a breast pump adapter;
a nipple adapter;
a nipple; and
a storage cap removably engageable with said liner, wherein said breast pump adapter removably engages said breast pump with said liner and said holder, and wherein said nipple adapter removably engages said nipple with said liner and said holder.

28. The system of claim 27, wherein said liner is a plurality of liners, each of said plurality of liners having a tapered cylindrical shape that allows stacking of said plurality of liners.

29. The system of claim 27, wherein said liner has a substantially cylindrical shape with an open end, wherein said holder has a substantially cylindrical shape with first and second open ends thereby forming a sleeve, and wherein said flexible liner is at least partially disposed in said holder.

* * * * *